United States Patent [19]

Beck et al.

[11] 3,968,142

[45] July 6, 1976

[54] HYDRONAPHTHALENE CARBOXYLIC ACIDS AND DERIVATIVES

[75] Inventors: Dieter Beck, Basel; Karl Schenker, Binningen; Alberto Rossi, Oberwil, all of Switzerland

[73] Assignee: Ciba-Geigy Corporation, Ardsley, N.Y.

[22] Filed: Oct. 7, 1969

[21] Appl. No.: 864,543

[30] Foreign Application Priority Data

Oct. 16, 1968 Switzerland.................. 15455/68
July 3, 1969 Switzerland.................. 10201/69
Sept. 2, 1969 Switzerland.................. 13261/69

[52] U.S. Cl. .................. 260/469; 260/465 R; 260/465 D; 260/465 G; 260/471 R; 260/473 F; 260/475 SC; 260/515 R; 260/515 A; 260/515 P; 260/518 R; 260/520 D; 260/544 R; 260/558 R; 260/558 A; 424/308; 424/309; 424/317; 424/319; 424/324
[51] Int. Cl.² .................................. C07C 69/95
[58] Field of Search ................. 260/469, 515

[56] References Cited
UNITED STATES PATENTS 3,502,697 3/1970 Woodward ................ 260/469
3,565,904 2/1971 Juby et al. ................ 260/469

OTHER PUBLICATIONS

Fujita et al., Agr. Biol. Chem., vol. 25, No. 9, pp. 710–718 (1961).

Chemical Abs. CIBA Ltd. vol. 68, col. 59449–59450.
Chemical Abs. Battelle Inst. vol. 63, col. 8327–8329.

*Primary Examiner*—James A. Patten
*Attorney, Agent, or Firm*—Joseph G. Kolodny; Theodore O. Groeger; John J. Maitner

[57] ABSTRACT

Compounds of the formula

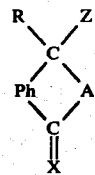

in which Ph represents an ortho-phenylene radical which contains in position 4 or 5 an unsubstituted or substituted hydrocarbon radical of aliphatic character, R represents a lower alkyl radical or especially a hydrogen atom, Z represents a free, esterified or amidated carboxyl group, A represents an ethylene radical and X stands for two hydrogen atoms or especially for an oxo group, are useful as chemotherapeutic and prophylactic agents against pain and inflammation.

19 Claims, No Drawings

HYDRONAPHTHALENE CARBOXYLIC ACIDS AND DERIVATIVES

SUMMARY OF THE INVENTION

The present invention relates to new bicyclic compounds. Especially it concerns compounds of the formula (I)
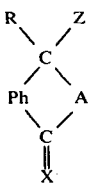

in which Ph represents an ortho-phenylene radical which contains in position 4 or 5 an unsubstituted or substituted hydrocarbon radical of aliphatic character, R represents a lower alkyl radical or especially a hydrogen atom, Z represents a free, esterified or amidated carboxyl group, A represents an ethylene radical and X stands for two hydrogen atoms or especially for an oxo group, and their salts, as well as pharmaceutical preparations containing those compounds and a process for treating pain and inflammation which consists in administering to a warm blooded being and pharmaceutical preparations.

The ortho-phenylene radical Ph, which contains in position 4 or 5 a hydrocarbon radical of aliphatic character, may contain further substituents. Thus, for example, when the said hydrocarbon radical is in position 4, it may contain in position 5, or when the said hydrocarbon radical is in position 5, in position 4, a hydrogen atom, an alkoxy radical, an amino, nitro or hydroxyl group or especially a halogen atom or a trifluoromethyl group. The radical Ph may further contain in position(s) 3 and/or 6 one of the substituents indicated for the positions 4 and 5, especially lower alkyl radicals, alkoxy radicals, halogen atoms or trifluoromethyl groups and especially hydrogen atoms.

The possibly substituted hydrocarbon radical of aliphatic character in position 6 or 7 of the new compounds is preferably in position 6.

The term hydrocarbon radicals of aliphatic character designates those radicals whose first member linked with the orthophenylene radical is not a member of an aromatic system.

Accordingly, suitable hydrocarbon radicals of aliphatic character are, for example, alkyl, alkenyl, alkinyl, cycloalkyl, cycloalkenyl, cycloalkyl-alkyl or -alkenyl radicals or cycloalkenyl-alkyl or -alkenyl radicals or arylalkyl or aralkenyl radicals, for example phenyl-lower alkyl or -alkenyl radicals and especially lower types of the said hydrocarbon radicals, where "lower" signifies those radicals which contain at most 7 carbon atoms.

Lower alkyl radicals are, for example, methyl, ethyl, propyl or isopropyl radicals, or linear or branched butyl, pentyl or hexyl radicals which may be linked in any desired position.

Lower alkenyl radicals are for instance allyl or methallyl radicals.

A lower alkinyl radical is especially a propargyl radical.

Cycloalkyl or -alkenyl radicals are for instance possibly lower alkylated cycloalkyl or cycloalkenyl radicals containing 4 to 7, especially 5 to 7, ring members, for example possibly lower alkylated cyclopentyl, cyclohexyl, cycloheptyl, cyclopentenyl, cyclohexenyl such as 1- or 3-cyclohexenyl or cycloheptenyl radicals. Preferred cycloalkenyl radicals are 1-cycloalkenyl radicals.

Cycloalkyl-alkyl radicals or -alkenyl radicals are in the first place those with lower alkyl or alkenyl radicals, especially with those mentioned above, in the first place those with the above-mentioned cycloalkyl radicals, such as 1- or 2-cyclopentyl-ethyl, 1-, 2- or 3-cyclohexyl-propyl, cycloheptyl-methyl or 1- or 2-cyclohexyl-ethenyl groups.

Cycloalkenyl-alkyl or -alkenyl radicals preferably contain lower alkyls or alkenyls, especially those mentioned above and primarily the above-mentioned cycloalkenyl radicals such as 1- or 2-cyclopent-3-enyl-ethyl, 1- or 2-cyclohex-1-enyl-ethyl, cyclohept-1-enyl-methyl or 1or 2-cyclohex-3-enyl-ethenyl groups.

As phenyl-lower alkylradicals there may be mentioned for instance 1- or 2-phenylethyl radicals or benzyl radicals whose phenyl nucleus may be substituted, for example, by lower alkyl or alkoxy radicals, halogen atoms, trifluoromethyl or similar radicals.

Phenyl-lower alkenyl radicals are, for example, 1-or 2-phenylethenyl radicals or cinnamyl radicals whose phenyl nucleus may be substituted like the phenyl-lower alkyl groups.

Alkoxy radicals are in the first place lower alkoxy radicals, for example methoxy, ethoxy, propoxy, isopropoxy, butoxy or amyloxy groups, and suitable halogen atoms are more especially fluorine, chlorine or bromine atoms.

Esterified carboxylic groups are especially those which are esterified with aliphatic, cycloaliphatic or araliphatic alcohols. Esterifying alcohols are more especially lower alkanols, cycloalkanols or phenylalkanols which may contain further substituents, for example methanol, ethanol, propanol, butanol, hexanols, cyclopentanols, cyclohexanols or phenyl-lower alkanols which may be substituted for instance as shown above for the phenyl-lower alkyl radicals, such as benzyl alcohols or phenylethanols.

An ethylene radical A is for instance an ethylene radical substituted by one or several lower alkyl radicals, especially those mentioned above or especially an unsubstituted ethylene radical.

The new compounds possess valuable pharmacological properties, especially an analgesic, such as antinociceptive (Writhing) activity as well as an anti-inflammatory effect. Thus, for example, on oral administration of 30 to 200 mg/kg in the Writhing syndrom test on the mouse they produce a distinct inhibition on the development of the syndrome, and on oral administration of 30 to 200 mg/kg in the kaolin oedema test on the rat paw a distinct anti-inflammatory activity. The new compounds therefore are useful as analgesics and antiphlogistics.

The new compounds are also valuable intermediates for the manufacture of other useful substances, especially of pharmacologically active compounds.

Specially valuable are the compounds of the general formula (II) 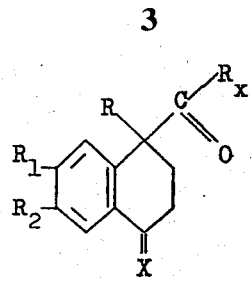

(V) 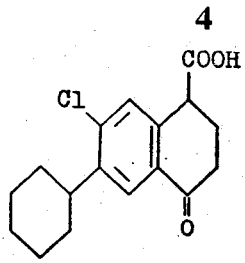

in which R and X have the above meanings, either $R_1$ or $R_2$, preferably $R_2$, represents a lower alkyl radical or especially a lower alkenyl, cycloalky-alkyl, cycloalkenyl or especially cycloalkyl radical and the other a hydrogen atom or especially a halogen atom or a trifluoromethyl group, and $R_x$ represents a lower alkoxy group such as an alkoxy group having 1–6 carbon atoms, for example a methoxy or ethoxy group, a free amino group or especially a hydroxyl group.

Special mention because of their good anti-inflammatory and analgesic (antinociceptive) activity deserve the compounds of the general formula (III)

in which R and X have the above meanings, either $R_3$ or $R_4$, preferably $R_4$, represents a lower alkyl radical, or especially a lower alkenyl, cycloalkyl-alkyl, cycloalkenyl or above all cycloalkyl-radical and the other a halogen atom or a trifluoromethyl group, and $R_y$ represents a lower alkoxy group such as an alkoxy group having 1 to 6 carbon atoms, for example a methoxy or ethoxy group, or especially a hydroxyl group.

Specially valuable are the compounds of the general formula (IV)

in which either $R_5$ or $R_6$, preferably $R_6$, is a lower alkyl radical or especially a lower alkenyl, cycloalkyl-alkyl, cycloalkenyl or above all cycloalkyl radical and the other is a chlorine or bromine atom, and $R_z$ represents a hydroxyl group or a lower alkoxy group, especially one that contains at most 4 carbon atoms, and more especially the 4-oxo-6-cyclohexyl-7-chloro-1,2,3,4-tetrahydronaphthalene-1-carboxylic acid of the formula which an oral administration of 30 mg/kg in the Writhing syndrome test on the mouse produces a distinct antinociceptive effect and on oral administration of 30 mg/kg in the kaolin oedema test on the rat paw produces a distinct anti-inflammatory effect.

The new compounds can be prepared by methods known per se.

In a preferred variant a compound of the formula (VI)
$$H-Ph-\underset{Z_1-A}{\overset{R}{\underset{|}{C}}}-Z$$

in which Ph, R, Z and A have the above meanings and $Z_1$ represents a free or esterified carboxyl group is cyclized, advantageously with a condensing agent to form a compound of the general formula (VII) 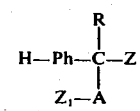

in which Ph, R, Z and A have the above meanings and, if desired, the 4-oxo group is reduced to two hydrogen atoms.

The condensing agent is preferably in anhydrous condensing agent, especially 100% sulfuric acid.

The reaction is performed in the usual manner, at an elevated temperature or preferably at room temperature but for a longer reaction time.

The new compounds are also obtained when in a compound of the formula (VIa)

in which Ph, R, A, and X have the above meanings, the cyano group is hydrolyzed or alcoholysed to form a free, esterified or amidated carboxyl group.

The hydrolysis leading to the amidated or free carboxyl group is carried out in known manner, for example in the presence of a strong acid, for example a mineral acid such as sulfonic acid or hydrochloric acid and, in the hydrolysis to the free carboxyl group, with addition of an oxidant such as nitrous acid.

The alcoholysis leading to an esterified carboxyl group is carried out in the usual manner, for example by reaction with an appropriate alcohol, for example in the presence of a mineral acid such as sulfuric acid, and advantageously in the presence of ammonium chloride.

In resulting compounds substituents may be introduced, modified or eliminated to suit the definition of the final products.

A 4-oxo group may be reduced in known manner, for example by the Huang-Minlon modification of the Wolff-Kishner method by heating a 4-oxo compound with hydrazine and an alkali metal hydroxide, such as sodium hydroxide, in a high-boiling solvent, for example di- or triethyleneglycol, and distilling off the water formed.

Furthermore, residues Z in resulting compounds may be converted into one another.

Esterified carboxyl groups and amidated carboxyl groups, that is to say carbamyl groups, can be converted into free carboxl groups in the usual manner, for example by hydrolysis, preferably in the presence of a strong base or strong acid, for example those mentioned above. If desired, an oxidant, such as nitrous acid, may be additionally used in the hydrolysis of carbamyl groups.

Free or esterified carboxyl groups may be converted into carbamyl groups in the usual manner, for example by reaction with ammonia and possibly dehydration of the intermediately formed ammonium salt.

Free carboxyl groups can be esterified in known manner, for example by reaction with an appropriate alcohol, advantageously in the presence of an acid such as a mineral acid, or by reaction with an appropriate diazo compound, for example a diazoalkane.

Free carboxy groups can be converted also for instance in the usual manner into acid halide groupings, for example by reaction with halides or phosphorus or sulfur such as thionylchloride, phosphorus pentachloride or tribromide. The acid halide group can then be converted into esterified carboxyl groups or carbamyl groups in the usual manner by reaction with appropriate alcohols, if desired in the presence of an acid acceptor such as an organic or inorganic base or with ammonia.

Furthermore, a double bond in a hydrocarbon radical in position(s) 6 or 7 and/or 5 and/or 8 of a resulting compound may be hydrogenated, for example with catalytically activated hydrogen.

Depending on the starting materials and reaction conditions used acid final products are obtained, that is to say those in which X represents a free carboxyl group, in free form or in form of their salts with bases. Resulting free acid compounds can be converted in the usual manner, for example by reaction with suitable bases, into salts with bases, especially into therapeutically acceptable salts with bases, for example salts with organic amines or metal salts. Suitable metal salts are primarily alkali or alkaline earth metal salts, such as sodium, potassium, magnesium or calcium salts. From the salts the free acids can be liberated in the usual manner, for example by reaction with acid reagents. The salts may also be used for purifying the new compounds, for example by converting the free compounds into their salts, isolating the salts and reconverting them into the free compounds. In view of the close relationship between the new compounds in free form and in form of their salts what has been said above and hereinafter with reference to the free compounds concerns also the corresponding salts wherever possible and suitable.

Depending on the chosen starting materials and reaction conditions and the number of asymmetric carbon atoms the new compounds may be obtained as optical antipodes, racemates or isomer mixtures (racemate mixtures).

A resulting isomer mixture (racemate mixture) may be resolved on the bases of the physico-chemical differences of the constituents into the two stereoisomeric (diastereomeric) pure racemates, for example by chromatography and/or fractional crystallization.

Resulting racemates can be resolved into the diastereomers by known methods, for example by recrystallization from an optically active solvent, or with the aid of microorganisms, or by reaction of a free carboxylic acid with an optically active base capable of forming salts with the racemic compound and separation of the salts thus obtained, for example on the strength of their different solubilities, and from the diastereomers thus separated the antipodes can be obtained by treatment with a suitable reagent. A particularly frequently used optically active base is, for example, the D- and L-form of cinchonine. It is advantageous to isolate the more active of the two antipodes.

The invention includes also any variant of the process in which an intermediate obtained at any stage of the process is used as starting material and any remaining step(s) is/are carried out, or in which a starting material is formed under the reaction conditions and is processes in situ, or in which a reactant may be in form of a salt thereof. Thus, for example, a compound of the general formula VI, in which Y represents a nitrile group, may be cyclized, and the water liberated during the cyclization transforms the nitrile group into the amide group.

The reactions of this invention are advantageously carried out with starting materials that give rise to the groups of final products specially mentioned above and more especially the specifically described or emphasized final products.

The starting materials are known or, insofar as they are new, they are accessible by known methods. New starting materials are likewise included in this invention.

The invention is specially also concerned with the starting materials of the general formula (IX) 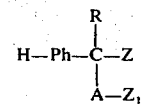

in which Ph, R, Z, $Z_1$ and A have the above meanings, esterified hydroxyl groups $Z_1$ being particularly those mentioned above. These compounds have the effects described for the final products and therefore are useful as analgesics and antiphlogistics.

Specially valuable are the compounds of the general formula (X) 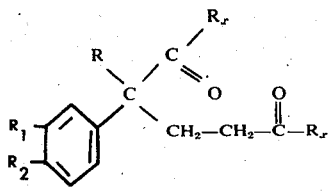

in which R, $R_1$, $R_2$ and $R_x$ have the above meanings and $R'_x$ represents a lower alkoxy group such as an alkoxy group having 1–6 carbon atoms, for example a methoxy or ethoxy group, or especially a hydroxyl group.

Specially valuable because of their good anti-inflammatory and analgesic (antinociceptive) effects are the compounds of the general formula (XI) 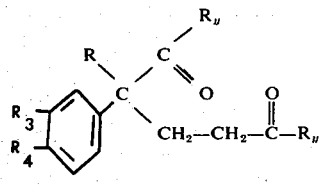

in which R, $R_3$, $R_4$ and $R_y$ have the above meanings.

Of special value are the compounds of the general formula (XII) 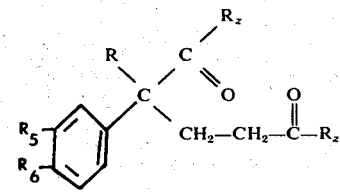

in which R, $R_5$, $R_6$ and $R_z$ have the above meanings, and more especially the 2-(3-chloro-4-cyclohexyl-phenyl)-glutaric acid and in the first place the 3-chloro-4-cyclohexyl-α-(2-carboxyethyl)-hydratropic acid, both of which produce in the kaolin oedema test on the rat paw on oral administration a distinct anti-inflammatory activity.

These starting materials in their turn are obtained from substances that are known, or insofar as they are new, are accessible by methods known per se.

For example, the new starting materials of the general formula IX result when in a compound of the formula (XIII) 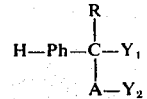

in which Ph, R and A have the above meanings and at least of the one radicals $Y_1$ and $Y_2$ is a cyano group and the other radical may also be a free, esterified or amidated carboxyl group, the cyano group(s) is/are hydrolysed or alcoholized to form a free, esterified or amidated carboxyl group, and in resulting compounds in which $Y_2$ stands for a carbamyl group, the carbamyl group is converted into a free carboxyl group.

The above reactions are preferably performed in the manner described for the manufacture of the final products.

According to a preferred route the new starting materials of the general formula IX are obtained when a compound of the formula (XVI) 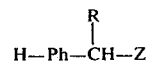

in which Ph, R and Z have the above meanings, is reacted with a suitable, possibly lower alkylated, acrylic acid derivative, especially with acrylonitrile or an acrylic acid ester, and if an acrylonitrile is used, in the resulting compound the cyano group is hydrolysed or alcoholysed to form a free or esterified carboxyl group. It is advantageous to perform the reaction in the presence of a condensing agent, for example benzyl trimethyl ammonium hydroxide. The reaction may be performed at room temperature or with heating.

In resulting starting materials substituents may be introduced, modified or eliminated to suit the definition of the starting materials. This can be done more especially in the manner described for the final products.

The subsequent reactions may be performed individually or in combination and in any desired order of sequence. The above-mentioned reactions are carried out by known methods, in the presence or absence of diluents, preferably those which are inert towards and dissolve the reagents, catalysts, condensing agents and/or in an inert atmosphere, at room temperature or with cooling or heating, under atmospheric or superatmospheric pressure.

Anything said here relating to the final products insofar as acid compounds and salts, optical antipodes, racemates and isomer mixtures, manufacture from the intermediates, termination of processes, formation of starting materials in situ and the salt-form of starting materials are concerned, is equally applicable to the new starting materials.

For the performance of the reactions according to this invention for the manufacture of the new starting materials of the general formula IX it is advantageous to use substances that furnish the specially mentioned groups of the new starting materials and especially the specifically described or emphasized new starting materials.

The pharmacologically active compounds can be used, for example, in form of pharmaceutical preparations containing them in free form or, if desired, in form of their salts, especially the therapeutically acceptable salts, in conjunction or admixture with a pharmaceutical organic or inorganic, solid or liquid excipient suitable, for example, for enteral or parenteral administration. Suitable excipients are substances that do not react with the new compounds, for example water, gelatin, lactose, starches, stearyl alcohol, magnesium stearate, talcum, vegetable oils, benzyl alcohols, gums, propyleneglycols, white petroleum jelly or other known medicinal excipients. The pharmaceutical preparations may be, for example, tablets, dragees, capsules or suppositories, or in liquid form solutions (for example elixirs or syrups), suspensions or emulsions. They may be sterilized and/or contain assistants such as preserving, stabilizing, wetting or emulsifying agents, solubilizers, salts for regulating the osmotic pressure or buffers. They may also contain further therapeutically valuable substances. The pharmaceutical preparations are formulated in the usual manner.

The new compounds can also be used in veterinary medicine, for example in one of the above-mentioned forms or in form of animal feedingstuffs or of additives to animal feedingstuffs, using for instance the conventional extenders and diluents and, respectively, feedingstuffs.

The following Examples illustrate the invention.

EXAMPLE 1

With thorough cooling 13.6 g of 3-chloro-4-cyclohexyl-α-(2-carboxyethyl)-hydratropic acid are dissolved in 70 ml of 100% sulfuric acid and the solution is kept over-night at room temperature, then cautiously poured out over ice and the aqueous mixture is extracted with ethyl acetate and the extract is evaporated. The resulting crystals are recrystallized from acetone, to yield 11.5 g of 1-methyl-4-oxo-6-cyclohexyl-7-chloro-1,2,3,4-tetrahydronaphthalene-1-carboxylic acid, melting at 227°–228°C, of the formula

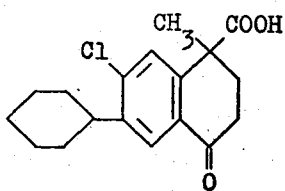

The 3-chloro-4-cyclohexyl-α-(2-carboxyethyl)-hydratropic acid used as starting material may be prepared in the following manner.

4.5 Grams of acrylonitrile are dropped into a solution of 18.5 g of 3-chloro-4-cyclohexyl-hydratropanitrile and 8 ml of a 35% methanolic solution of benzyl trimethyl ammonium hydroxide in 40 ml of ethanol at 20°–25°C, and the mixture is stirred overnight at room temperature. The solvent is then distilled off, the residue taken up in ethyl acetate, the solution is washed three times with water, dried over sodium sulfate and evaporated. The residual dark, viscous oil is distilled under a high vacuum, to yield 16.5 g of 3-chloro-4-cyclohexyl-α-(2-cyanoethyl)-hydratropanitrile boiling at 198°–200°C under 0.3 mm Hg pressure.

A mixture of 19.7 g of 3-chloro-4-cyclohexyl-α-(2-cyanoethyl)-hydratropanitrile, 33 ml of glacial acetic acid, 40 ml of concentrated sulfuric acid and 26 ml of water is refluxed overnight, then poured into water and the aqueous mixture is extracted with ethyl acetate. After having been dried and evaporated, the ethyl acetate solution leaves a dark resinous substance which is taken up in 300 ml of boiling toluene. From this solution there are obtained 17.5 g of crystalline 3-chloro-4-cyclohexyl-α-(2-carboxyethyl)-hydratropic acid melting at 173°–175°C, corresponding to the formula

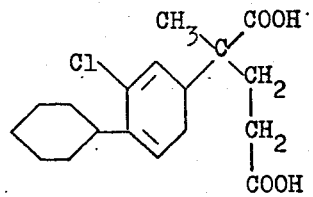

EXAMPLE 2

A mixture of 6.7 g of 1-methyl-4-oxo-6-cyclohexyl-7-chloro-1,2,3,4-tetrahydronaphthalene-1-carboxylic acid, 4 g of hydrazine hydrate, 6.7 g of potassium hydroxide and 40 ml of triethyleneglycol is heated for 2 hours at 130°–140°C. Then, while distilling off a mixture of hydrazine and water, the temperature is raised to 195°C and the batch is stirred until nitrogen is no longer being given off, then diluted with 50 ml of water, acidified with concentrated hydrochloric acid and the mixture is extracted with ethyl acetate. The ethyl acetate is evaporated and the residual crude product recrystallized from acetone; to yield 5.9 g of 1-methyl-6-cyclohexyl-7-chloro-1,2,3,4-tetrahydronaphthalene-1-carboxylic acid melting at 167°–168°C, of the formula

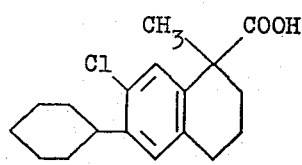

EXAMPLE 3

While cooling well, 17.9 g of 2-(3-chloro-4-cyclohexylphenyl)-glutaric acid are dissolved in 90 ml of 100% sulfuric acid and the solution is kept overnight at 35°C, then cautiously poured out over ice and the aqueous mixture is extracted with ethyl acetate and evaporated. The remaining crystals are recrystallized from toluene, to yield 12.2 g of 4-oxo-6-cyclohexyl-7-chloro-1,2,3,4-tetrahydronaphthalene-1-carboxylic acid melting at 204°–205°C, of the formula

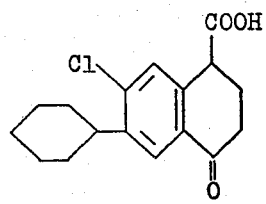

The 2-(3-chloro-4-cyclohexylphenyl)-glutaric acid used as starting material may be prepared thus:

A mixture of 11.5 g of 3-chloro-4-cyclohexylphenylacetonitrile, 15 ml of absolute ethanol and 5.3 ml of concentrated sulfuric acid is refluxed overnight, then diluted with water and several times extracted with ether. The ethereal solution is washed with sodium bicarbonate solution and water and dried over sodium sulfate, evaporated, and the residue is distilled under a high vacuum, to yield 12.5 g of 3-chloro-4-cyclohexylphenylacetic acid ethyl ester boiling at 137° to 139°C under 0.3 mm Hg pressure.

A mixture of 40.5 g of 3-chloro-4-cyclohexylphenylacetic acid ethyl ester and 16 g of acrylic acid ethyl ester is added dropwise to a solution of 3.6 g of sodium in 60 ml of ethanol. The solution is refluxed overnight and then poured into a mixture of 10 ml of glacial acetic acid and 170 ml of ice water. The ethanol is distilled off and the residue extracted with ethyl acetate and evaporated; the residue is distilled under a high vacuum, to yield 24.3 g of 2-(3-chloro-4-cyclohexylphenyl)-glutaric acid diethyl ester boiling at 203°–205°C under 0.4 mm Hg pressure.

A solution of 28.3 g of 2-(3-chloro-4-cyclohexylphenyl)-glutaric acid diethyl ester in 450 ml of ethanol is mixed with 165 ml of N-sodium hydroxide solution and the whole is kept overnight at room temperature, then the ethanol is evaporated under vacuum; the aqueous solution is extracted once with ethyl acetate which is discarded, and 165 ml of N-hydrochloric acid are added. The aqueous mixture is extracted with ethyl acetate, dried and evaporated to leave a resinous substance which is taken up in boiling toluene. From this solution 18 g of 2-(3-chloro-4-cyclohexylphenyl)-glutaric acid melting at 140° to 142 °C crystallize out; it corresponds to the formula

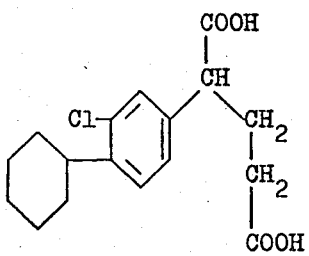

EXAMPLE 4

A mixture of 6 g of 4-oxo-6-cyclohexyl-7-chloro-1,2,3,4-tetrahydronaphthalene-1-carboxylic acid, 4 g of hydrazine hydrate, 6.4 g of potassium hydroxide and 40 ml of triethyleneglycol is heated for 2 hours at 130°–140°C. Then, while distilling off a mixture of hydrazine and water, the temperature is raised to 195°C and the batch is stirred until nitrogen is no longer being given off, then diluted with 50 ml of water, acidified with concentrated hydrochloric acid and the mixture is extracted with ethyl acetate and the ethyl acetate is evaporated. The resulting crude product is recrystallized from toluene, to yield 4.5 g of 6-cyclohexyl-7-chloro-1,2,3,4-tetrahydronaphthalene-1-carboxylic acid melting at 119°–120°, of the formula

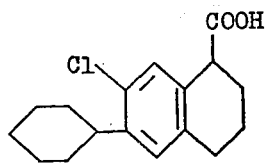

EXAMPLE 5

A solution of 18 g of para-cyclohexyl-α-(2-carboxyethyl)-hydratropic acid in 90 ml of 100% sulfuric acid is stirred at 30°–40°C for 6hours, then carefully poured on to ice, and the aqueous mixture is extracted with chloroform. On evaporation of the chloroform, a resinous mass is obtained, which is dissolved in toluene. From the resulting solution, 1-methyl-4-oxo-6-cyclohexyl-1,2,3,4-tetrahydronaphthalene-1-carboxylic acid of the formula

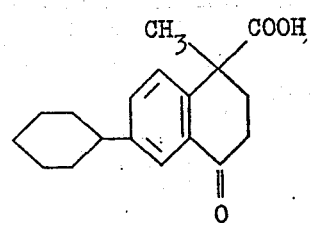

crystallizes. Melting point, 165°–167°C.

The para-cyclohexyl-α-(2-carboxyethyl)-hydratropic acid used as starting material can be prepared as follows:

While cooling well, a solution of 2.5 g of sodium borohydride in 10 ml of water is added dropwise to a solution of 20.2 g of para-cyclohexyl-acetophenone in 250 ml of methanol. The mixture is stirred at room temperature for 1 hour and the pH then adjusted to 2 with semi-concentrated hydrochloric acid. The batch is evaporated completely and the residue extracted several times with ether. The solution is dried and the ether evaporated to obtain methyl-(para-cyclohexylphenyl)-carbinol in the form of colorless crystals melting at 81°–83°C.

25 ml of thionyl chloride are added dropwise to a solution of 20.4 g of methyl-(para-cyclohexylphenyl)-carbinol in 100 ml of benzene and 3 ml of pyridine, and the mixture then refluxed for 5 hours. It is then poured on to ice, the aqueous mixture is extracted with ether, and the ethereal solution washed with sodium bicarbonate solution and water. When the solution is dried and the ether evaporated, α-methyl-para-cyclohexylbenzyl chloride is obtained in the form of a dark viscous liquid which is processed directly.

To a mixture, heated at 90°C, of 6 g of sodium cyanide and 30 ml of dimethylsulfoxide, a solution of 22.2 g of α-methyl-para-cyclohexylbenzyl chloride in 30 ml of dimethylsulfoxide are added dropwise at such a rate that the temperature does not exceed 100°C. After that, the batch is stirred for another hour at 100°C and then poured into water. The aqueous mixture is extracted with ethyl acetate. The solution is dried and the solvent evaporated, and a dark oil obtained which is distilled in a high vacuum. There is obtained in this manner para-cyclohexyl-hydratropanitrile boiling at 136°–137°C under a pressure of 0.25 mm of Hg.

At 20°–25°C, 4.35 g of acrylonitrile are added dropwise to a solution of 16 g of para-cyclohexyl-hydratropanitrile and 7 ml of Triton B in 40 ml of ethanol. The mixture is then stirred at room temperature overnight. The solvent is distilled off, the residue dissolved in ethyl acetate, the solution washed three times with water, dried over sodium sulfate, and the solvent evaporated. The residual, dark, viscous oil is distilled in a high vacuum. There is thus obtained paracyclohexyl-α-(2-cyanethyl)-hydratropanitrile boiling at 193°–196°C under a pressure of 0.4 mm of Hg.

A mixture of 21 g of para-cyclohexyl-α-(2-cyanethyl)-hydratropanitrile, 40 ml of glacial acetic acid, 48 ml of concentrated sulfuric acid, and 32 ml of water is refluxed overnight. It is then poured into water, and the aqueous mixture extracted with ethyl acetate. When the ethyl acetate solution is dried and evaporated, a dark, resin-like mass is obtained, which is dissolved in 200 ml of toluene. From this solution, 12.8 g of para-cyclohexyl-α-(2-carboxyethyl)-hydratropic acid crystallize. Melting point, 174°–175°C.

EXAMPLE 6

A mixture of 12 g of l-methyl-4-oxo-6-cyclohexyl-1,2,3,4-tetrahydronaphthalene-1-carboxylic acid, 10 g of hydrazine hydrate, 13.7 g of potassium hydroxide, and 85 ml of triethylene glycol is heated at 130°–140°C for 2 hours. After that, while distilling off a mixture of hydrazine and water, the temperature is raised up to 195°C, and the batch is stirred until the evolution of nitrogen ceases. The mixture is then diluted with 50 ml of water, acidified with concentrated hydrochloric acid, then extracted with ethyl acetate. The resin-like crude product remaining after evaporation of the ethyl acetate is crystallized from toluene and yields 1-methyl-6-cyclohexyl-1,2,3,4-tetrahydronaphthalene-1carboxylic acid of the formula

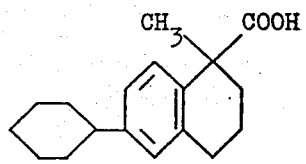

melting at 128°–129°C.

EXAMPLE 7

While cooling well, 12.8 g of 2-(para-cyclohexylphenyl)-glutaric acid are dissolved in 65 ml of 100% sulfuric acid and the solution allowed to stand overnight at room temperature. It is then carefully poured on to ice, and the aqueous mixture extracted with ethyl acetate. On evaporation of the ethyl acetate, 4-oxo-6-cyclohexyl-1,2,3,4-tetrahydronaphthalene-1-carboxylic acid of the formula

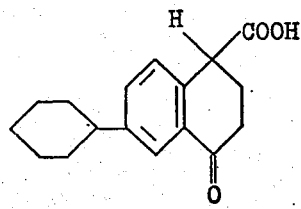

is obtained.

The 2-(para-cyclohexyl-phenyl)-glutaric acid used as starting material can be prepared as follows:

In an autoclave, a mixture of 20.2 g of para-cyclohexylacetophenone, 6.4 g of sulfur, 25 ml of concentrated aqueous ammonia, and 15 ml of pyridine is heated at 165°C for 4½ hours. The reaction product is dissolved in methylene chloride, the methylene chloride solution is washed with dilute hydrochloric acid and water, dried over sodium sulfate, and the solvent evaporated. The residue is digested with 100 ml of carbon disulfide, filtered with suction, and recrystallized from ethyl acetate. There is obtained paracyclohexyl-phenylacetamide melting at 167°–168°C.

17.3 g of para-cyclohexyl-phenylacetamide and 35 ml of thionyl chloride are stirred at 70°C for 3 hours. The excess thionyl chloride is evaporated, the residue dissolved in ethyl acetate, and the solution washed with sodium bicarbonate solution and water. The solvent is evaporated and the residue distilled in a high vacuum. There is obtained paracyclohexylphenylacetonitrile boiling at 131°–132°C under a pressure of 0.35 mm of Hg and melting at 48°–49°C.

13.7 g of para-cyclohexyl-phenylacetonitrile, 21 ml of absolute ethanol, and 7.3 ml of concentrated sulfuric acid are boiled overnight. The mixture is then diluted with water and extracted several times with ethyl acetate. The solution is washed with sodium bicarbonate solution and water, and dried over sodium sulfate. The residue obtained on evaporation of the solvent is distilled in a high vacuum. There is obtained para-cyclohexylphenyl acetic acid ethyl ester boiling at 125°–127°C under a pressure of 0.5 mm of Hg.

A mixture of 15 g of para-cyclohexyl-phenylacetic acid ethyl ester and 6.7 g of acrylic acid ethyl ester is added dropwise to a solution of 1.5 g of sodium in 25 ml of ethanol. The solution is boiled overnight and then poured into a mixture of 5 ml of glacial acetic acid and 75 ml of water. The alcohol is distilled off and the batch extracted with ethyl acetate. The residue remaining on evaporation of the ethyl acetate is distilled in a high vacuum. There is obtained 2-(para-cyclohexylphenyl)-glutaric acid diethyl ester boiling at 184°–186°C under a pressure of 0.4 mm of Hg.

47 g of 2-(para-cyclohexylphenyl)-glutaric acid ethyl ester are dissolved in 350 ml of ethanol, 300 ml of 1N-sodium hydroxide solution are added, and the mixture stirred at room temperature overnight. The alcohol is then evaporated under vacuum, the aqueous solution extracted twice with ethyl acetate, which is discarded, and 300 ml of 1N-hydrochloric acid are added. The aqueous mixture is extracted with ethyl acetate. After drying and evaporation of the ethyl acetate, a resin-like mass is obtained which is dissolved in a little boiling toluene. From the resulting solution, 2-(para-cyclohexylphenyl)-glutaric acid crystallizes. It melts at 104°–107°C.

EXAMPLE 8

A mixture of 12.2 g of 4-oxo-6-cyclohexyl-1,2,3,4-tetrahydronaphthalene-1-carboxylic acid, 9.1 g of hydrazine hydrate, 14.5 g of potassium hydroxide and 100 ml of triethylene glycol are heated at 130°–140°C for two hours. While distilling off a hydrazine-water mixture, the temperature is raised up to 195°C and the batch is stirred until the evolution of nitrogen ceases. The batch is diluted with 100 ml of water, acidified with concentrated hydrochloric acid, and the mixture extracted with ethyl acetate. After evaporation of the ethyl acetate, 6-cyclohexyl-1,2,3,4-tetrahydronaphthalene-1-carboxylic acid of the formula

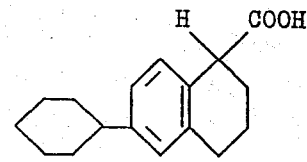

remains behind.

EXAMPLE 9

A mixture of 19 g of 4-cyano-6-chloro-7-cyclohexyl-3,4-dihydro-naphthalene-1(2H)-one, 36 ml of glacial acetic acid, 43 ml of concentrated sulfuric acid, and 29 ml of water is refluxed overnight. It is then poured into water, and the aqueous mixture is extracted with ethyl acetate. After drying and evaporation of the solvent, the residue is crystallized from toluene. There are obtained 14.3 g of 4-oxo-6-cyclohexyl-7-chloro-1,2,3,4-tetrahydro-naphthalene-1-carboxylic acid melting at 204°–205°C, which product is identical with the compound of Example 3.

The 4-cyano-6-chloro-7-cyclohexyl-3,4-dihydronaphthalene-1(2H)-one used as starting material can be obtained in the following manner.

To a solution of 2.5 g of sodium in 50 ml of ethanol there is added dropwise a mixture of 23.4 g of 3-chloro-4-cyclohexyl-phenylacetonitrile and 10 g of acrylic acid ethyl ester. The solution is boiled overnight and then poured into a mixture of 10 ml of glacial acetic acid and 150 ml of water. The ethanol is evaporated and the residue distilled in a high vacuum to obtain 4-(3-chloro-4-cyclohexylphenyl)-4-cyano-butyric acid ethyl ester boiling at 200°–203°C under a pressure of 0.35 mm of Hg.

26.6 g of 4-(3-chloro-4-cyclohexylphenyl)-4-cyanobutyric acid ethyl ester are dissolved in 300 ml of ethanol, and to the resulting solution are added 80 ml of 1N-sodium hydroxide solution, and the mixture is allowed to stand at room temperature overnight. The ethanol is then evaporated under reduced pressure, the aqueous solution extracted once with ethyl acetate, which is discarded, and 80 ml of 1N-hydrochloric acid are added. The aqueous mixture is extracted with ethyl acetate. After drying and evaporation of the ethyl acetate solution, 4-(3-chloro-4-cyclohexylphenyl)-4-cyano-butyric acid remains as a resin-like mass which is processed directly.

25 ml of thionyl chloride are added to a solution of 23 g of 4-(3-chloro-4-cyclohexyl-phenyl)-4-cyano-butyric acid in 100 ml of benzene, and the mixture is heated at 60°C for 3 hours. On evaporation, 4-(3-chloro-4-cyclohexyl-phenyl)-4-cyano-butyric acid chloride remains as a dark liquid which is processed immediately.

24 g of 4-(3-chloro-4-cyclohexylphenyl)-4-cyano-butyric acid chloride, dissolved in carbon disulfide, are added to a mixture of 15 g of tin tetrachloride and 150 ml of carbon disulfide while cooling well. The reaction mixture is allowed to stand at room temperature for 15 hours, then poured on to ice and hydrochloric acid. The organic phase is separated, and the aqueous layer extracted twice more with ethyl acetate. On drying and evaporation of the solvent, 4-cyano-6-chloro-7-cyclohexyl-3,4-dihydronaphthalene-1(2H)-one remains as a resin-like mass, which is used as starting material without prior purification.

EXAMPLE 10

23 g of 4-oxo-6-cyclohexyl-7-chloro-1,2,3,4-tetrahydronaphthalene-1-carboxylic acid are dissolved in 100 ml of ethanol and 80 ml of benzene, and after the addition of 0.5 ml of concentrated sulfuric acid the mixture is boiled with the use of a water separator until all reaction water is removed. The batch is diluted with ether, the solution washed with sodium bicarbonate solution and water, and dried over sodium sulfate. After elimination of the solvent, the residue is distilled under a high vacuum, and 4-oxo-6-cyclohexyl-7-chloro-1,2,3,4-tetrahydronaphthalene-1-carboxylic acid ethyl ester of the formula

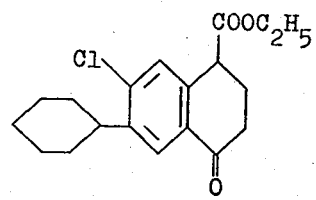

obtained which boils at 184°–191°C under a pressure of 0.04 mm Hg.

EXAMPLE 11

A mixture of 16 g of 4-oxo-6-cyclohexyl-7-chloro-1,2,3,4-tetrahydronaphthalene-1carboxylic acid, 45 g of cyclohexanol and 500 ml of benzene is saturated with dry hydrogen chloride gas. While passing in a slow current of hydrogen chloride gas, the benzene is distilled off over the course of 3 to 4 hours. The residue is dissolved in ether and the solution washed with sodium bicarbonate solution and water. The solution is dried over sodium sulfate, the solvent and excess cyclohexanol are eliminated in vacuo, and 4-oxo-6-cyclohexyl-7-chloro-1,2,3,4-tetrahydro-1-naphthalene-1-carboxylic acid-cyclohexyl ester of the formula

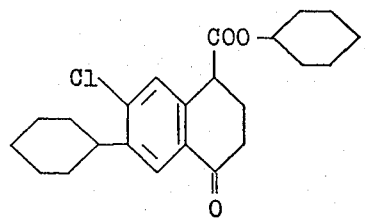

obtained as a highly viscous oil.

In an analogous manner as described in Examples 1, 3, 5 and 7 there may be obtained also 4-oxo-6-isopropyl-7-chloro-1,2,3,4-tetrahydro-1-naphthalene-1-carboxylic acid.

EXAMPLE 12

Tablets containing 100 mg of 4-oxo-6-cyclohexyl-7-chloro-1,2,3,4-tetrahydro-napthalene-1-carboxylic acid may be prepared with the following ingredients:

| | Per tablet |
|---|---|
| 4-oxo-6-cyclohexyl-7-chloro-1,2,3,4-tetrahydro-naphthalene-1-carboxylic acid | 100 mg |
| lactose | 50 mg |
| wheat starch | 73 mg |
| colloidal silicid acid | 13 mg |
| talc | 12 mg |
| magnesium stearate | 2 mg |
| | 250 mg |

METHOD

The active substance is mixed with the lactose, part of the wheat starch, and with colloidal silicic acid, and the mixture passed through a sieve. Another portion of the wheat starch is pasted with the five-fold quantity of water on a water bath, and the powder mixture is kneaded with the paste until a slightly plastic mass is obtained. The mass is forced through an about 3 mm mesh sieve, dried, and the dry granulate is again passed through a sieve. Then the remainder of the wheat starch, talc and magnesium stearate are admixed. The resulting mixture is compressed into tablets of 250 mg each.

EXAMPLE 13

In an analogous manner as described in the Example 1–11 the following compounds may be prepared:

1-butyl-3-methyl-4-oxo-6-cyclopentyl-7,8-dichloro-1,2,3,4-tetrahydronaphthalene-1-carboxylic acid amide;
2-ethyl-5-methoxy-6-cycloheptyl-1,2,3,4-tetrahydronaphthalene-1-carboxylic acid benzyl ester;
3-isopropyl-6-cyclohexyl-7-trifluoromethyl-1,2,3,4-tetrahydronaphthalene-1-carboxylic acid amide;

4-oxo-5,8-dibromo-6-cyclohexenyl-1,2,3,4-tetrahydronaphthalene-1-carboxylic acid p-chlorobenzyl ester;
1-ethyl-7-(4-methyl-cyclohexyl)-8-fluoro-1,2,3,4-tetrahydronaphthalene-1-carboxylic acid p-methoxybenzyl ester;
5-methyl-6-benzyl-1,2,3,4-tetrahydronaphthalene-1-carboxylic acid;
4-oxo-6-alkyl-1,2,3,4-tetrahydronaphthalene-1-carboxylic acid;
4-oxo-6-trifluoromethyl-7-propargyl-1,2,3,4-tetrahydronaphthalene-1-carboxylic acid;
6-cyclohexylmethyl-7-chloro-1,2,3,4-tetrahydronaphthalene-1-carboxylic acid phenethyl ester;
4-oxo-6-(2-cyclopentylethyl)-7-bromo-1,2,3,4-tetrahydronaphthalene-1-carboxylic acid;
4-oxo-7-(2-cyclohexyl-ethenyl)-8-ethoxy-1,2,3,4-tetrahydronaphthalene-1-carboxylic acid;
6-(1-cyclohexenylmethyl)-7-chloro-1,2,3,4-tetrahydronaphthalene-1-carboxylic acid methyl ester;
6-(2-cyclohex-3-enyl-ethenyl)-7-chloro-1,2,3,4-tetrahydronaphthalene-1-carboxylic acid;
7-(p-chlorobenzyl)-8-chloro-1,2,3,4-tetrahydronaphthalene-1-carboxylic acid;
4-oxo-6-[1-(p-methoxy-phenyl)-ethyl]-1,2,3,4-tetrahydronaphthalene-1-carboxylic acid.

We claim:
1. A member selected from the group consisting of the formula

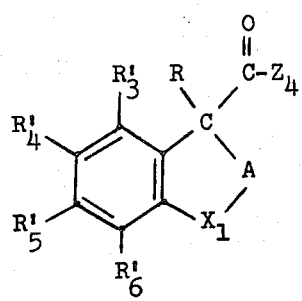

in which $Z_4$ stands for a member selected from the group consisting of hydroxy and lower alkoxy, R stands for a member selected from the group consisting of hydrogen and lower alkyl, $X_1$ stands for a member selected from the group consisting of carbonyl and methylene, A stands for 1,2-ethylene $R_3'$ and $R_6'$ each stands for hydrogen, either of the radicals $R_4'$ and $R_5'$ stands for a member selected from the group consisting of lower cycloalkyl and lower cycloalkenyl, and the other one of the radicals $R_4'$ and $R_5'$ stands for a member selected from the group consisting of hydrogen, halogen and trifluoromethyl, and a pharmaceutically acceptable, nontoxic salt thereof.

2. A product as claimed in claim 1, in which $Z_4$ stands for a member selected from the group consisting of hydroxy and alkoxy having 1–6 carbon atoms, each of R, $X_1$ A, $R_3'$ and $R_6'$ has the meaning given in claim 28, one of the radicals $R_4'$ and $R_5'$ stands for a member selected from the group consisting of lower cycloalkyl and lower cycloalkenyl and the other one of the radicals $R_4'$ and $R_5'$ stands for a member selected from the group consisting of halogen and trifluoromethyl.

3. A product as claimed in claim 1, in which $Z_4$ stands for a member selected from the group consisting of hydroxy or alkoxy having at most 4 carbon atoms, R stands for hydrogen, A stands for 1,2-ethylene, $R_3'$ and $R_6'$ each stands for hydrogen, $X_1$ stands for carbonyl, $R_4'$ stands for a member selected from the group consisting of chlorine and bromine and $R_5'$ stands for lower cycloalkyl.

4. A product as claimed in claim 1, in which $Z_4$ stands for hydroxy, R stands for a member selected from the group consisting of hydrogen and methyl, A stands for 1,2-ethylene, $R_3'$ and $R_6'$ each stands for hydrogen, $R_4'$ stands for a member selected from the group consisting of hydrogen and chlorine and $R_5'$ stands for cyclohexyl.

5. A compound as claimed in claim 1, said compound being 4-oxo-6-cyclohexyl-7-chloro-1,2,3,4-tetrahydronaphthalene-1-carboxylic acid.

6. A compound as claimed in claim 1, said compound being a member selected from the group consisting of ethylester and cyclohexylester of 4-oxo-6-cyclohexyl-7-chloro-1,2,3,4-tetrahydronaphthalene-1-carboxylic acid.

7. A compound having the formula

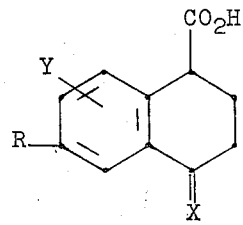

wherein X is $H_2$ or O, R is cyclohexyl, and Y is hydrogen, chloro, bromo, fluoro, hydroxy, (lower)alkyl, (lower)alkoxy, nitro or amino; or a nontoxic, pharmaceutically acceptable salt thereof.

8. A compound of claim 7 wherein X is $H_2$.
9. A compound of claim 7 wherein X is O.
10. A compound of claim 7 having the formula

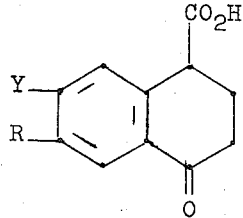

wherein R is cyclohexyl and Y is hydrogen, chloro, bromo, fluoro, hydroxy, (lower)alkyl, (lower)alkoxy, nitro or amino; or a nontoxic, pharmaceutically acceptable salt thereof.

11. A compound of claim 10 wherein R is cyclohexyl and Y is hydrogen, chloro, fluoro, hydroxy, (lower)alkyl, (lower)alkoxy, nitro or amino; or a pharmaceutically acceptable, nontoxic salt thereof.

12. A compound of claim 10 wherein R is cyclohexyl and Y is hydrogen, chloro, (lower)alkyl or (lower)alkoxy; or a pharmaceutically acceptable, nontoxic salt thereof.

13. A compound of claim 10 and being the 7-chloro-6-cyclohexyl-4-oxo-1,2,3,4-tetrahydro-1-naphthoic acid or a pharmaceutically acceptable, nontoxic salt thereof.

14. A compound of claim 10 and being the 6-cyclohexyl-4-oxo-1,2,3,4-tetrahydro-1-naphthoic acid or a pharmaceutically acceptable, nontoxic salt thereof.

15. A compound of claim 7 having the formula

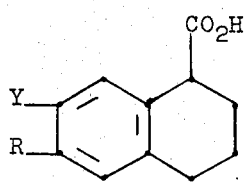

wherein R is cyclohexyl and Y is hydrogen, chloro, bromo, fluoro, hydroxy, (lower)alkyl, (lower)alkoxy, nitro or amino; or a nontoxic, pharmaceutically acceptable salt thereof.

16. A compound of claim 15 wherein R is cyclohexyl, and Y is hydrogen, chloro, fluoro, hydroxy, (lower)alkyl, (lower)alkoxy, nitro or amino; or a pharmaceutically acceptable, nontoxic salt thereof.

17. A compound of claim 15 wherein R is cyclohexyl and Y is hydrogen, chloro, (lower)alkyl or (lower)alkoxy; or a pharmaceutically acceptable, nontoxic salt thereof.

18. A compound of claim 15 and being the 7-chloro-6-cyclohexyl-1,2,3,4-tetrahydro-1-naphthoic acid or a pharmaceutically acceptable, nontoxic salt thereof.

19. A compound of claim 15 and being the 6-cyclohexyl-1,2,3,4-tetrahydro-1-naphthoic acid or a pharmaceutically acceptable, nontoxic salt thereof.

* * * * *